US007544926B2

(12) United States Patent
Resch-Genger et al.

(10) Patent No.: US 7,544,926 B2
(45) Date of Patent: Jun. 9, 2009

(54) MULTI-FUNCTIONAL CALIBRATION SYSTEM AND KIT, AND THEIR USES FOR CHARACTERIZING LUMINESCENCE MEASUREMENT SYSTEMS

(75) Inventors: Ute Resch-Genger, Berlin (DE); Katrin Hoffmann, Berlin (DE); Roland Nitschke, Gundelfingen (DE); Axel Engel, Ingelheim (DE)

(73) Assignee: Bam Bundesanstalt Fuer MaterialForschung und-Pruefung, Berlin (DE)

( * ) Notice: Subject to any disclaimer, the term of this patent is extended or adjusted under 35 U.S.C. 154(b) by 325 days.

(21) Appl. No.: 11/377,593

(22) Filed: Mar. 15, 2006

(65) Prior Publication Data

US 2007/0159624 A1 Jul. 12, 2007

(30) Foreign Application Priority Data

Mar. 18, 2005 (DE) ................ 10 2005 013 229
Oct. 11, 2005 (DE) ................ 10 2005 049 364

(51) Int. Cl.
*G12B 13/00* (2006.01)
(52) U.S. Cl. .................................. 250/252.1
(58) Field of Classification Search ........... 250/252.1
See application file for complete search history.

(56) References Cited

U.S. PATENT DOCUMENTS

| 6,635,487 B1 | 10/2003 | Lee et al. ............... 436/19 |
| 2003/0015668 A1* | 1/2003 | Montagu ............... 250/458.1 |
| 2003/0030797 A1 | 2/2003 | Palladino et al. ......... 356/243.1 |

FOREIGN PATENT DOCUMENTS

DE 10 2004 044 717 A1 3/2006

JP 2000-159543 6/2000

OTHER PUBLICATIONS

U. Resch-Genger et al.; "Traceability in Fluorometry: Part II. Spectral Fluorescence Standards"; May 2005, Journal of Fluorescence, vol. 15, No. 3, pp. 315-336.

U. Resch-Genger et al.; "How to Improve Quality Assurance in Fluorometry: Fluorescence-Inherent Sources of Error and Suited Fluorescence Standards"; May 2005; Journal of Fluorescence, vol. 15, No. 3, pp. 337-362.

R. A. Velapoldi and K.D. Mielenz; Standard Reference Materials: A Fluorescence Standard Reference Material: Quinine Sulfate Dihydrate; National Bureau of Standards Special Publication; U.S. Department of Commerce; Jan. 1980.

(Continued)

*Primary Examiner*—David P Porta
*Assistant Examiner*—Mindy Vu
(74) *Attorney, Agent, or Firm*—Norris McLaughlin & Marcus, PA (57) ABSTRACT

The invention relates to a multi-functional calibration system (10) for characterizing luminescence measurement systems, in particular spectrally resolving, wide-field and/or confocal imaging systems, with (a) a baseplate (12),
(b) at least one calibration module (24) arranged on the baseplate (12) and including at least one calibration and/or characterization function, and
(c) at least one focusing device (20) integrated in the baseplate (12) with a focusing surface (22) for setting a defined measurement beam focus of the luminescence measurement systems to be calibrated, the focusing surface (22) arranged in a common plane with the at least one calibration module (24).

17 Claims, 2 Drawing Sheets

OTHER PUBLICATIONS

Ambler Thompson and Kenneth L. Eckerle; "National Insitute of Standards and Technology"; Fluorescence Detection III, SPIE, vol. 1054, 1989, pp. 20-25.

J. W. Hofstraat and M.G. Latuhihin; "Correction of Fluorescence Spectra"; Applied Spectroscopy, vol. 48, No. 4, 1994, pp. 436-446.

J.A. Gardecki and M. Maroncelli; "Set of Secondary Emission Standards for Calibration of the Spectral Responsivity in Emission Spectroscopy"; Applied Spectroscopy; vol. 52, No. 9, 1998, pp. 1179-1189.

Jean-Christophe Roulet, et al.; "Performance of an Integrated Microoptical System for Fluorescence Detection in Microfluidic Systems"; Analytical Chemistry, vol. 74, No. 14, Jul. 15, 2002; pp. 3400-3407.

* cited by examiner

MULTI-FUNCTIONAL CALIBRATION SYSTEM AND KIT, AND THEIR USES FOR CHARACTERIZING LUMINESCENCE MEASUREMENT SYSTEMS

The invention relates to a multi-functional calibration system for characterizing luminescence measurement systems, in particular spectrally resolved, wide-field and/or confocal imaging systems, a kit that includes the multi-functional calibration system and uses of the calibration system and the kit.

Photoluminescence measurement systems include an excitation channel with, for example, an excitation light source and a wavelength-selective optical component, and an emission channel typically arranged perpendicular to the optical path of the excitation light, which is used to measure the light emitted by the chromophore in the sample space after light absorption (photoluminescence). A certain portion of the excitation light is typically coupled to a reference channel through a beam splitter which includes an optical component, such as a mirror or a scatterer and a (reference) detector. The reference channel is used to record the actual excitation light intensity at the excitation wavelength for capturing temporary variations in the excitation light intensity.

Each luminescence measurement technique supplies measurement data composed of contributions specific for the analyte and for the system. The undesirable system-specific contributions represent a wavelength and polarization dependence of system components of the employed measurement system. These dependencies are caused, in particular, by the optical components in the excitation and emission channel of the system, the excitation light source and the employed detection systems. These system-specific contributions have to be determined so as to be able to compare luminescence data across different systems and laboratories, to determine aging of the system, as a requirement for traceability of luminescence data to radiometric primary standards (according to the requirements of EN ISI/IEC 17025), as well as to draw quantitative conclusions about the fluorescence, to determine relative fluorescence quantum yields and to optimize luminescence methods. This applies particularly to comparative evaluations of wavelength-shifted luminescence profiles or to emission measurements at different excitation wavelengths.

The aforementioned system-specific contributions to the fluorescence signal can be measured by determining so-called emission and excitation correction functions, which describe the spectral sensitivity of the employed detection systems and the wavelength dependence of the spectral illumination intensity or the excitation light intensity at the sample location for the emission and the excitation channel of the respective system. Fluorescence measurement systems generally also require determination of the linearity of the detection system(s), in particular for system calibration and quantitative fluorescence measurements, for characterizing the long-term stability and the day-to-day performance of the system, as well as the uniformity of the illumination, and for comparing measurement data acquired on different systems and in different laboratories. In spectrally resolved (confocal or wide-field) imaging systems, which have as detectors mostly PTMs, and to a lesser degree CCD-based detectors, other system parameters, such as the uniformity of the illumination, the spectral and the spatial resolution (x, y, z) must be determined. An important application of confocal microscopes with spectrally resolving detectors is the pixel-wise deconvolution of overlapping dye emissions in samples marked with several fluorescing dyes. No standard preparations are available to date to test robustness against interfering signals, such as poor signal-to-noise ratio, and to quantify the measurement accuracy at different concentrations.

The use of certified physical transfer standards for measuring system-specific effects is known. The excitation channel is typically calibrated with certified receiver standards, whereas the emission channel is calibrated with certified standard lamps. The use of physical transfer standards disadvantageously requires technical knowledge by the user in the field of optics, expensive recalibration, and is subject to changes in the spectral density due to the service life of the standard lamps. When standard lamps are used for emission correction, the different emission characteristics of lamp and sample and the difference in spectral radiance between the transfer normal and a typical luminescence sample must also be taken into account, which can be more than three orders of magnitude. So-called quantum counters are also used to measure the excitation correction. These are highly concentrated dye solutions which completely absorb light quanta and emit with a wavelength-independent fluorescence quantum yield. Quantum counters provide measurement data which depend on concentration and geometry and are also susceptive to polarization effects. Standardized calibration methods with defined concentrations in combination with defined measurement geometries are not available for quantum counters.

Also known are so-called fluorescence standards which are typically based on the photoluminescence of a chemical compound. Spectral fluorescence standards or so-called emission and excitation standards with known emission and excitation spectra, which have been corrected for system-specific effects, can be used to determine the spectral characteristics of photoluminescence measurement systems in the context of a system calibration. Such fluorescence standards are used in several forms, in particular in the form of solutions or embedded in solid polymer or glass matrices. Fluorescence standards have the advantage of having a similar luminescence intensity and emission characteristics as the measured luminescence samples. The last standards can hence be used to spectrally calibrate under typical conditions encountered in sample measurements. Fluorescence standards can be measured in many different types of systems, formats and measurement geometries and are therefore suitable also for calibrating fluorescence measurement systems with special sample geometries or formats, for example micro-cuvettes, micro-titer plates and cryostat systems. Only fluorescence standards permit calibration in the same cuvette and measurement arrangement as the actual sample measurement and thus provide optimized calibration results. All application-relevant properties of a transfer standard must be fully characterized before it can be used, including the applied method and information about the measurement accuracy and adequate long-term stability in a solid pure state or in solution, for example embedded in a matrix.

The published literature discusses in detail certain recommendations for fluorescence standards, which also apply to emission and excitation standards and fluorescence quantum yield standards (e.g., U. Resch-Genger et al., J. Fluoresc. 2005, 15(3), 315ff; U. Resch-Genger et al., J. Fluoresc. 2005, 15(3), 337ff). However, quinine sulfate dihydrate (SRM936) is thus far the only emission standard where the corrected emission spectrum has been certified by a government institution, in this case by the National Institute for Standards and Technology (NIST, U.S.A.), with a traceable characterized reference fluorometer with a known measurement accuracy (R. A. Velapoldi, K. D. Mielenz, NBS Spec. Publ. 1980, 260-264, PB 80132046, Springfield, Va.). Only for this standard is information available about dye purity, the measurement parameters used to calibrate the employed spectrometer, and the measurement accuracy. A combination of several chromophores with matched fluorescence spectra is required to calibrate a photoluminescence measurement system over the entire UV/vis/NIR spectral range. However, very few examples of standard combinations are known to date. Among those are, for example, combinations of emission standards, which consist of fluor-phosphor-containing polymer foils with NIST-certified emission spectra (A. Thompson, K. L. Eckerle, SPIE 1989, 1054, 20; J. W. Hofstraat & M. J. Latuhihin, Appl. Spectrosc. 1994, 48, 436). Also known as emission and excitation standards are fluor phosphor-containing polymethylmethacrylate (PMMA) blocks in form of cuvettes. A statistic approach for combining two partial correction functions of the different dye standards to a total correction functions using a counting rate statistics (Poisson statistics) have been described by J. A. Gardecki and M. Maroncelli (Appl. Spectrosc. 1998, 52, 1179).

Several substances have insufficient photo-stability and form under typical excitation and measurement conditions photoproducts with their own spectral contributions. This applies in particular to their use in devices with high illumination intensity, in particular in laser-based measurement system and for confocal fluorescence microscopes. The low thermal and photochemical stability of most fluorescence standards designed for macroscopic applications limits their application for microscopes. The fluorescence anisotropy of many employed substances is too large and represents an additional error source during calibration and requires the use of polarizers. The produced spectra are mostly not traceable, information about the measurement accuracy is lacking and the spectra are certified by an authorized body only in exceptional cases (quinine sulfate dihydrate). Characterization of the application-relevant spectroscopic properties is frequently also incomplete, and information about the dye purity is often missing.

Not only are suitable dye standards for both spectral and quantitative calibration of photoluminescence measurement systems unavailable, but the system characterization of confocal spectral imaging systems is also difficult. In particular, different users may use different focus settings resulting in different probe depths in these measurements. This leads to poorly reproducible spectral effects replete with artifacts, caused by wall effects of the vessel and by the internal extinction effects in the dye. U.S. Pat. No. 6,635,487 B1 discloses a device for calibrating fluorescence measurement systems with micro-fluidic sample chambers, which uses a solid fluorescence standard. The measurement beam is focused outside the sample by a slit. US 2003/0030797 A describes a device for calibrating fluorescence readout devices for micro-titer plates and proposes to use solid fluorescence standards in the form of cavities of the titer plates. The inserts include, for example, an optical quartz or glass body which ideally has a low inherent fluorescence and is coated with a fluorescence material, for example quinine sulfate. No focusing aid is provided.

It is therefore an object of the invention to provide a device for a comprehensive characterization of luminescence measurement systems, in particular of spectrally resolving, confocal and/or wide-field imaging systems, which are easy to operate and allow a flexible and reproducible characterization of a large number of system parameters.

The object is solved by a calibration device with the features of claim 1. The multi-functional calibration system according to the invention for characterizing luminescence measurement systems, in particular spectrally resolved, wide-field and/or confocal imaging systems, includes (a) a baseplate, (b) at least one calibration module arranged on the baseplate and including at least one calibration and/or characterization function, and (c) at least one focusing device integrated in the baseplate with a focusing surface for setting a defined measurement beam focus of the luminescence measurement system to be calibrated, the focusing surface arranged in a common plane with the at least one calibration module.

The at least one integrated focusing aid enables a reliable focus settings of the measurement beam (excitation beam) which is identical for all users, and thereby also makes it possible to measure essentially identically illuminated measurement volumes on and inside the calibration modules of the calibration device. In this way, spectral effects caused by different measurement depths, such as wall effects or interior filter effects can be minimized and standardized. As a result, reproducible measurement data are generated which can be compared and traced across different systems and different laboratories.

According to the preferred embodiments, at least two focusing devices (focusing aids) are provided and integrated in the baseplate. The two focusing devices are preferably distributed over the baseplate, in particular arranged on opposing marginal regions of the baseplate. The flatness or a deviation from the flatness can also be determined and compensated for the measurement locations of the calibration modules by numerical interpolation.

The focusing aid device can be implemented in different ways. The focusing device basically includes an almost ideally flat focusing plane with a roughness that is significantly less than the optical resolution of the luminescence measurement system to be calibrated. Preferably, the focusing device includes a substantially flat substrate, such as a wafer made of a silicon single crystal or the like, on which a very thin layer of a reflecting and/or fluorescing material is sputtered. This can be, for example, a thin metal layer (e.g., chromium layer) with a thickness between 10 and 100 nm, in particular between 30 and 50 nm. Alternatively or in addition, the focusing plane can be lumenescing, in particular fluorescing. Preferred in addition to the typical fluorescing materials are quantum dots which have a particularly high photo-thermal stability. Particularly advantageous are different fluorescing materials arranged on the same wafer or on different wafers with different spectral properties that cover the typical excitation or emission spectral range of the respective measurement system. The focusing device can then also be used to determine the parfocality (parfocality means that the specimen stays in focus when the objective is changed) of an employed objective of the measurement system, so that the parfocal image can be adjusted by computational methods or by using auxiliary lenses in the microscope.

According to a particularly advantageous embodiment of the invention, the at least one calibration module can be positioned releasably on the baseplate, for example inserted into suitable receptacles of the baseplate. In this way, the calibration device can be flexibly adapted to different types of devices, measurement geometries, or calibration or characterization tasks. For example, inserts could be provided for determining the spectral sensitivity, the linearity of the detector, the uniformity of the illumination, the day-to-day performance, the spectral resolution and/or the spatial resolution. To maintain a constant dimension of the baseplate and the inserts in the x, y, and z-direction, materials with a small thermal expansion are used for these components. Suitable are in particular glass and glass ceramic materials with a linear thermal expansion coefficient $\alpha$ of less than $5 \times 10^{-6}$ K$^{-1}$ at room temperature. Suitable, but less preferred, are polymers with thermal expansion coefficient fluorescent sα of typically less than $5 \times 10^{-6}$ K$^{-1}$.

The dimensions (size of the baseplate, size and spacing of the calibration modules and focusing devices) and material (glass, quartz glass, plastic) and the design and positioning of the focusing device(s) and the calibration module(s) of the calibration system are adapted to the luminescence measurement system to be calibrated, for example to a spectrally resolving wide-field imaging system or a spectrally resolving confocal fluorescence microscope. For applications in the context of calibrations of spectrally resolving, confocal fluorescence microscopes, the focusing aids can be integrated, for example on both sides of a calibration device having the typical dimensions of microscope slides, so that each user measures an almost identical illuminated volume. This allows a comparative and reproducible device characterization and thus also of measurement data under measurement conditions that are relevant for the application and specific to the samples.

The invention also relates to a kit with a baseplate and at least one focusing device according to the description above, as well as a set with different calibration modules having different calibration and/or characterization functions. With the kit, users can adapt the calibration device to the particular individual requirements. The kit can include additional components, such as corrected (ideally: certified) fluorescence spectra of fluorescence standards contained in the calibration modules in digital form or an operating manual.

Several advantageous calibration modules of the calibration device and of the kit, respectively, will now be described in detail.

According to a preferred embodiment of the invention, the calibration device includes at least one calibration module for determining the spectral sensitivity, the wavelength accuracy, the linearity and/or the dynamic range of a detector system, the day-to-day performance (intensity standard) and/or for determining the illumination uniformity of the light source of the luminescence measurement system. All these functions can be implemented with at least one material comprising a fluorophore. The term "fluorophore" is meant to broadly encompass any substances (atoms, ions or compounds) which could emit a characteristic fluorescence signal after suitable excitation. These include in addition to the classic organic fluorescing compounds also quantum dots discussed above within the context of the focusing surfaces, and other fluorescing nanocrystals as well as ions of the rare-earth metals and transition metals. The fluorophore is preferably contained in an optically transparent matrix, i.e., the calibration module is an optically transparent material doped with a fluorophore, such as glass, glass ceramics or a plastic material. The distribution of the fluorophore in the matrix should be very homogeneous so that position-independent fluorescence spectra up to the maximum spatial resolution of the measurement system can be obtained. A module containing a fluorophore can generally also be used in time-resolved measurements as a fluorescence lifetime standard.

According to a particularly advantageous embodiment of the invention, the at least one calibration module for determining the spectral sensitivity includes an optically transparent base material made of a lanthanum phosphate glass, a fluor phosphate glass, a fluor crown glass, a lanthanum glass, a glass ceramics formed of these glasses, or a lithium aluminum silicate glass ceramics. This basic glass material is preferably doped with at least one element, a particular a metal ion, selected from the group of the rare-earth metals (including scandium, yttrium, lanthanum and the lanthanides), in particular the lanthanides (comprising the 14 elements with the atomic number 58 to 71). Preferred are hereby cerium (Ce), europium (Eu), terbium (Te), thulium (Tm), erbium (Er), and samarium (Sm). Advantageously, these elements or a mixture thereof in the form of oxides according to the formula $M_2O_3$ are added to the glasses. The aforementioned rare-earth metals have structured narrow band spectra. According to another preferred embodiment, the aforementioned base materials are doped with at least one metal ion selected from the group of the transition metals, such as cobalt (Co), chromium (Cr), and manganese (Mn), as well as others.

A matrix of an organic polymer (plastic) or particularly silicate is preferred for use with classic organic fluorophores. A transparent base material for quantum dots or other fluorescing nanocrystals can be glasses, glass ceramics, or plastics.

Another functional type of preferred calibration modules includes modules for determining the (absolute) excitation light intensity for standardizing the calibration modules. These include, for example, a scatterer which reflects incoming light diffusely into all spatial directions, or bleachable fluorophores with a known bleaching kinetics, for example a glass or plastic matrix doped with such fluorophore. Scatterers, for example translucent glass objects, can also be used as a calibration module for determining the suppression of the excitation wavelength in the emission channel of the luminescence measurement system.

Another calibration module advantageously provided in the calibration device or the kit is a module for determining the spatial resolution in the x, y and/or z-direction and/or of the illumination uniformity. A reflecting and/or fluorescing surface, preferably a reflecting or fluorescing inclined plane, can be employed for this function. Alternatively or in addition, a three-dimensionally structured plane, preferably with a fluorescing coating, can be used as calibration module for determining the spatial resolution in the plane and/or as a function of depth.

The calibration device according to the invention or the kit, depending on the modular construction, can be used for a large number of calibration and/or characterization applications, in particular for the functions described in the context of the calibration modules.

The calibration device or the kit can also be used as a fluorescence intensity standard for determining relative fluorescence intensities in the UV/vis/NIR spectral range, i.e., for the quantitative calibration of intensities. The calibration device can also be used to characterize the long-term stability and day-to-day instrument performance variations of the measurement intensities of the measurement system and to compare luminescence measurement systems. Additional applications are the characterization of the uniformity of the illumination at different excitation and emission wavelengths, the use as fluorescence lifetime standard, the possibility to compare luminescence data and intensities, the determination of the relative spectral illumination intensity at the sample location and the spectral deconvolution of chromophore mixtures, and the testing of evaluation software used for these tasks. The calibration device or the kit is particular suited to perform the aforedescribed applications in a typical application wavelength range of 200 to 2500 nm, preferably in the UV/vis/NIR range from 350 to 850 nm.

Additional preferred embodiments of the invention are recited as additional features in the dependent claims.

Exemplary embodiments of the invention will now be described with reference to the corresponding drawings.

Figure 1A:
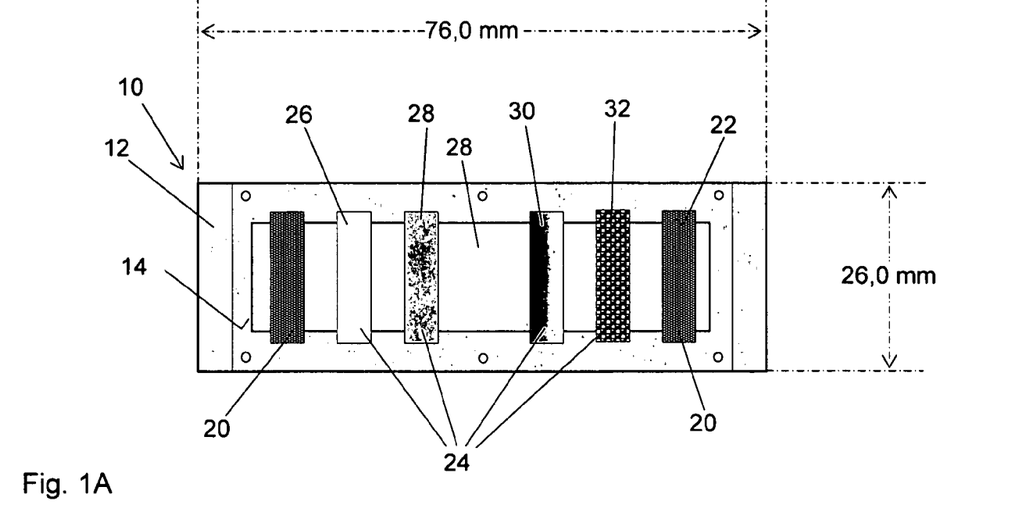
FIG. 1A shows a top view of a multi-functional calibration system according to the invention without a cover glass.
Figure 1B:
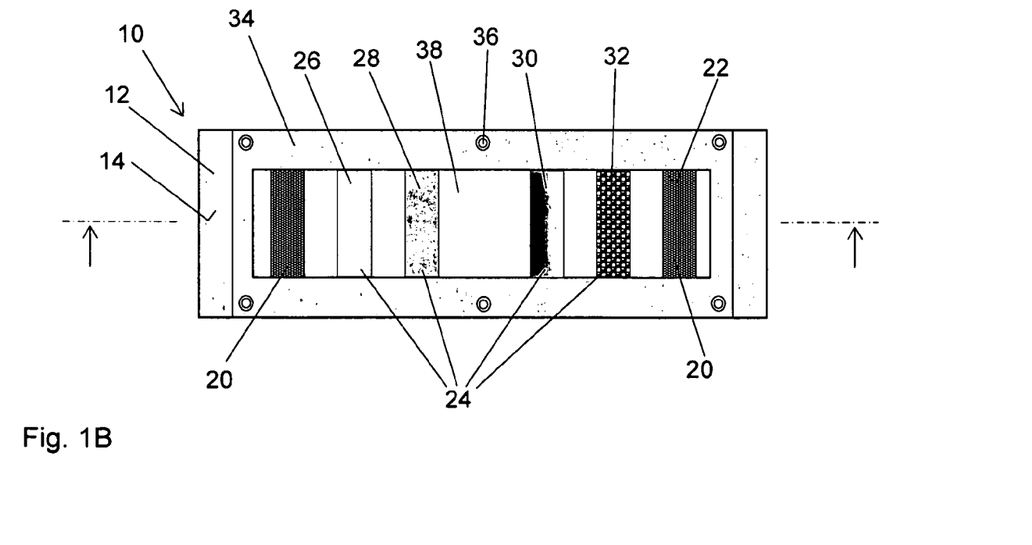
FIG. 1B shows a top view of the calibration system of FIG. 1A with applied cover glass.
Figure 1C:
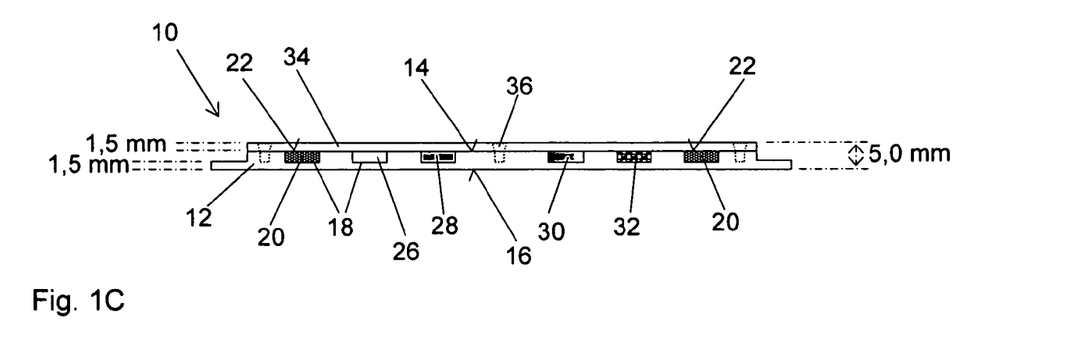
FIG. 1C shows a longitudinal cross-section of the calibration system along the sectional line indicated in FIG. 1B.

FIGS. 1A to 1C show different views of a multi-functional calibration system indicated with the reference symbol 10 according to an advantageous embodiment of the invention for calibrating, in particular, a confocal fluorescence microscope. The calibration system 10 includes a two-dimensional baseplate 12 with a topside 14 and a bottom side 16. The baseplate 10 can be constructed of a suitable polymer, glass or quartz glass and can be made in one-piece or in several pieces, also by using different materials. The dimensions of the baseplate 12 in the depicted embodiments are 76.0 mm×26.0 mm and therefore correspond to standard dimensions of microscope slides for microscopes. A plurality of, in this case six, receptacles 18 in form of a rectangular material depressions are provided on the topside 14 of the baseplate 12 (FIG. 1C). A focusing device 20 is arranged in the outer two receptacles 18, i.e., at the opposing marginal regions of the baseplate 12. In an alternative embodiment, more than two focusing devices 20 can be distributed on the baseplate 12, or only a single focusing device may be employed. If only one focusing device 20 is provided, then this focusing device 20 is preferably arranged in the center region of the baseplate 12. The focusing devices 20 each have a focusing surface 22, which in the depicted embodiment is at the top.

In the depicted example, the focusing devices 20 are implemented as highly planar wafers made of silicon single crystals which have a respective reflecting focusing surface 22. The focusing surface 22 consists of a thin layer of chromium sputtered onto the wafer which forms the substrate. The chromium layer has a layer thickness of 40 nm. The roughness of the focusing surface is significantly less than the optical resolution of the luminescence microscope to be calibrated. Other wafer materials or reflecting metal layers are also feasible. Alternatively, the focusing devices can also include highly planar lumenescing focusing surfaces 22. These can be implemented, for example, as very thin layers of fluorescing semiconductor nanoparticles, so-called quantum dots, consisting of several hundred to several thousand atoms, which are deposited on a silicon wafer or the like by, for example, spin sputtering. Known fluorescing materials for quantum dots are, for example, cadmium-selenide, cadmium-telluride, indium-phosphide, lead-selenide, and others. Optionally, the quantum dots can be coated with a cover layer. Compared to conventional fluorescing material, quantum dots are advantageously very stable and resist bleaching. The layer thickness of the fluorescing focusing surface 22 preferably corresponds to a mono-layer of quantum dots and is therefore, for example, in a range of 7 to 10 nm. In other fluorescing or reflecting substances, the layer thickness is preferably only a few atomic or molecular layers of the respective material, preferably mono-atomic.

Different calibration modules 24, which each have at least one calibration function and/or a function for characterizing the luminescence measurement system, are inserted in the other receptacles 18. As seen in FIG. 1C, the focusing surfaces 22 of the focusing devices 20 are arranged in the same plane as the surfaces of the calibration modules 24. The calibration modules 24 and the focusing devices 20 also have a defined equidistant spacing from each other. In a preferred embodiment, the calibration modules 24 are loosely inserted into the receptacles 18 in the form of inserts. The modules 24 can then be easily exchanged to modify the calibration device for different applications. The equipment can then be adapted to different calibration and characterization tasks, for example, to determine the spectral sensitivity of the measurement system, to determine the linearity or the dynamic range of the employed detector system, to determine the spectral resolution or the spatial solution, to determine the illumination uniformity, etc. The modular design of the calibration system and its format, its dimensions and the spacing of the modules 24 can be adapted to the different measurement systems and geometries, for example to confocal, spectrally resolving imaging systems, such as confocal fluorescence microscope and micro-array scanners, as well as wide-field fluorescence microscopes, Raman spectrometers and Raman microscopes. The insertion modules 24 can be selected and combined to flexibly adapt the modules to various tasks, for example to system-specific excitation wavelengths and detectable emission regions, to varying signals strength, fluorescence intensity and/or intensity ratios. Several preferred calibration modules 26, 28, 30, 32 will be described below in more detail. The calibration system 10 of the invention is easy to operate and designed for use by technically trained personnel.

As shown in FIGS. 1B and 1C, the baseplate 12 with the focusing devices 20 and the calibration modules 24 can also be completely or partially covered with a transparent cover slide 34, which can be connected to the baseplate, for example, by screw connections 76. Media corrected for the cover glass and/or immersion media can also be used. In the depicted embodiment, both the baseplate 12 (FIG. 1A) and the cover glass 34 include an inspection window 38. The other region shown in gray is obscured, for example, by a varnish layer or the like.

The modules 26 and 28 represent a first type of calibration modules 24 and are made of an optically transparent material (such as a glass, a glass ceramics or a transparent plastic) that is doped throughout its volume with a fluorophore. The fluorophores suitable for the following applications should be excitable by application-relevant light sources with spectroscopic properties described below, should have a sufficiently high luminescence quantum yield and a sufficiently small fluorescence anisotropy, as well as an adequate homogeneity of the chromophore distribution and a high thermal and photo-chemical stability under application-relevant conditions.

According to an advantageous embodiment of the invention, the calibration module 26 is an optically transparent material which is doped with a metal ion selected from the group of the rare earth metals, in particular the lanthanides, or a mixture thereof. In the present example, the calibration module 26 is a lanthanum glass (e.g., 9% $Al_2O_3$, 70% $P_2O_5$, 8% $K_2O$, 13% $La_2O_3$), which is singly or multiply doped with a total of 1 to 6% of at least one lanthanide oxide, in particular $Ce_2O_3$, $Eu_2O_3$, $Tb_2O_3$, $Tm_2O_3$. Due to the narrow-band, highly structured spectra of the lanthanides, the calibration module 26 can be used in particular for determining the spectral resolution by checking if two spectrally close adjacent bands can still be resolved. The wavelength accuracy of the measurement system can also be checked by comparing the known position of the bands with their measure positions. The calibration module can also be used for determining the spectral sensitivity, i.e., the combination of wavelength and intensity accuracy as a function of wavelength, by comparing the intensity ratios of the selected emission bands.

The calibration module 28, which is also doped with a fluorophore, is preferably doped with a transition metal ion. This can be, for example, a lanthanum phosphate glass (see above) doped with 0.1 to 0.01% $Cr_2O_3$ or a lanthanum glass (30-60% $La_2O_3$, 30-50% $B_2O_3$, 1-5% $SiO_2$, 2-10% CaO) doped with 1 to 15% ZnO. Due to its broad-band, weakly structured spectra, the calibration module 28 doped with a transition metal is particularly suited for determining the spectral sensitivity of the detection system over a wide spectral range.

Both calibration modules 26, 28 can advantageously also used for checking the uniformity of the illumination. The intensity on the respective measurement surface is checked at selected wavelengths in the x, y-dimension to determine if the same intensity is measured at the center of the illuminated surface as in the marginal regions. Determining the illumination uniformity is very important in all spatially resolving imaging methods to correctly interpret and process intensity differences at different image positions. The calibration modules 26, 28 can also be used to characterize the long-term stability, to validate the performance, and to compare different systems. Both allow conclusions about the effect of device parameters on the generated fluorescence signals, for example the pinhole size (in confocal imaging systems and fluorescence microscope) or the PMT voltage (in confocal imaging systems, fluorescence microscope or micro-array reading devices). According to another embodiment (not shown), a number of calibration modules are provided which are doped with different concentrations of the same fluorophore. Such concentration series enables the determination of the linearity of the emission channel of the detector system, i.e., the intensity range over which the detector signal increases linearly with the received intensity, i.e., where a reliable quantitative statement can be made about the concentration of a chromophore in the sample. The concentration series can also be used to determine the dynamic range of the detector system, i.e., the smallest and the greatest detectable light intensity. The detector response resulting from a change in the amplification can also be determined.

The calibration module 30 represents an insert with an inclined plane, i.e., a plane that is inclined relative to the baseplate 12, which is either reflecting (as a mirror) or fluorescing. The aforedescribed materials for the focusing services 22 can in principle also be used as reflecting or fluorescing layers. The calibration module 30 with the inclined plane allows the measurement of the spatial resolution in the z-dimension by moving the measurement beam, with known slope of the plane, by a defined step width in the x, y-dimension while continuously focusing the beam (z-dimension), while observing changes in the reflection or fluorescence signal. The spatial resolution in the x, y-direction can be determined in the same way. In an alternative, but less preferred embodiment, the spatial resolution in the z-dimension can be determined with a simple (not inclined) reflecting or fluorescing plane in reflection mode with a z-scan. Such reflecting or fluorescing surface can also be used for determining the illumination uniformity.

A fourth calibration module 32 in the depicted example is an object with a three-dimensional structured surface, which is again coated with a fluorescing or reflecting layer. Such object can also be used for determining the spatial resolution in the x,y and/or z-direction. For example, if the surface has a saw tooth profile with a tooth height of 1 µm, then the signal measured at the highest point can be compared with the signal measured at the lowest point. If these two signals deviate from each other, then the z-resolution is at least 1 µm or better.

Preferred materials for the aforedescribed modules 24, in particular for the modules used to determine the spatial resolution in the x,y and/or z-direction of a photoluminescence measurement system and for the baseplate 12 are materials with a very low thermal expansion coefficient, in particular glass and glass ceramics materials, which have a linear thermal expansion coefficient $\alpha$ less than $5\times10^{-6}$ $K^{-1}$ at room temperature. This allows a reliable verification of the measured spatial resolution.

Another module (not shown) can be used to measure the excitation light intensity. For this purpose, for example, a polymer film can be used which is doped with a bleachable fluorophore with a known intensity-dependent bleaching kinetics. The incident light intensity can be determined by illuminating this film with the radiation source to be characterized and measuring the bleaching kinetics. The polymer film doped with a bleachable fluorophore is preferably provided with a x,y-coordinate matrix to determine the location of the excitation light on the object. More preferably, a scatterer, for example a translucent glass object, is used to determine the excitation light, which diffusely reflects the incoming light into all spatial directions, with a small fraction directed to the detector. If the percentage scattered by the scatterer is known, then the measurement of the intensity measured at the detector is a measure of the incoming excitation light intensity. A determination of the absolute excitation light intensity allows standardization of the excitation across different devices and laboratories. The translucent glass object (scatterer) can also be used to determine the quality of the suppression of the excitation wavelength in the emission channel, in particular in confocal, spectrally resolving imaging systems. This is done by illuminating the object, which itself does not fluoresce, with the corresponding excitation wavelength, and by measuring with the detection system the quantity of the excitation light which is scattered into the emission channel and is not suppressed by the filters in the emission channel. Preferably, the excitation light intensities required for typical fluorescence applications and the PMT sensitivity or camera exposure time can then be adjusted.

The fluorescence microscope is focused with the focusing devices 20 according to the invention in the following manner. The calibration system 10 is first positioned on a microscope stage of the fluorescence microscope. The measurement beam (excitation beam) of the system is then moved with the microscope stage, which can be adjusted with a motor in three dimensions, to one of the focusing devices 20 in the x,y-direction. (Alternatively, depending on the design of the microscope, the excitation beam can also be moved to the desired measurement location of the system by the adjustable optics while the fixed microscope stage remains fixed). The beam is then focused exactly on the focusing surface 22 of the focusing device 20 in the z-direction by moving the microscope stage with a motor in the z-direction (or the optics of the microscope is adjusted accordingly). The position is then determined where the maximum reflection signal (or fluorescence signal for a fluorescing focusing surface 22) is detected. This process can be performed completely automatically. The detected focus setting is stored as z-coordinate, or as frontal separation between the sample (focusing surface 22) and the front lens of the optics. If several focusing devices 20 are used, the same process is employed with the other focusing devices 20. Different focus settings (z-coordinates or frontal separations) for the different focusing devices 20 imply that the baseplate 12 is not completely planar. The z-coordinates for the x, y-positions of the calibration modules 24 arranged between the focusing devices 20 can then be numerically interpolated. The measurement beam is then sequentially moved to the corresponding calibration modules 24 and focused on the respective stored or interpolated z-coordinate. If the measurement is to be performed exactly on the surface of the respective calibration module 24, for example if the focusing surface is a mirror, then the required focus setting corresponds to the setting determined at the focusing surface 22. However, if a volume is to be measured at a certain depth, for example a depth of 30 μm, as is the case for a translucent glass object or for the glass modules 16, 28 doped with a fluorophore, then the focus of the optics is corrected by that depth with respect to the determined zero-focus setting for the respective calibration module. The focus determination with the focusing devices 20 therefore serves as a reference value for the corresponding surfaces of the calibration module 24. With the integrated focusing devices 20, the same sample volumes are always measured in each calibration module 24 of the calibration system 10, in particular in transparent, fluorophore-doped or scattering modules, even for different devices and across laboratories boundaries. Spectral effects caused by different measurement depths in the modules 24, for example by wall and internal filter effects, are thereby standardized and provide comparable and traceable measurement and calibration results.

LIST OF REFERENCE MATERIALS 10 calibration system
12 baseplate
14 topside
16 bottom side
18 receptacle
20 focusing device
22 focusing surface
24 calibration module
26 rare-earth-metal doped calibration module
28 transition-metal doped calibration module
30 calibration module with incline, reflecting and fluorescing plane
32 three-dimensionally structured calibration module
34 cover glass
36 screw connection
38 inspection window

The invention claimed is:

1. Multi-functional calibration system (10) for characterizing luminescence measurement systems, in particular spectrally resolving, wide-field and/or confocal imaging systems, comprising
(a) a baseplate (12),
(b) at least one calibration module (24) arranged on the baseplate (12) and including at least one calibration and/or characterization function, and
(c) at least one focusing device (20) integrated in the baseplate (12) with a highly planar focusing surface (22) having reflecting and/or lumenescing properties for setting a defined measurement beam focus of the luminescence measurement systems to be calibrated, the focusing surface (22) arranged in a common plane with the at least one calibration module (24) and having a surface roughness less than the optical resolution of the luminescence measurement system.

2. Calibration system (10) according to claim 1, characterized in that at least two focusing devices (20) integrated in the baseplate (12) are provided, which are arranged in particular on opposing marginal regions of the baseplate (12).

3. Calibration system (10) according to claim 1, characterized in that a plurality of calibration includes (24) having different functions is arranged on the baseplate (12).

4. Calibration system (10) according to claim 1, characterized in that the at least one calibration module (24) is a module for determining the spectral sensitivity, the wavelength accuracy, the linearity and/or the dynamic range of a detector system and/or for determining the illumination uniformity of the light source of the luminescence measurement system.

5. Calibration system (10) according to claim 4, characterized in that the at least one calibration module (24) is at least one material comprising a fluorophore, in particular an optically transparent material doped with a fluorophore.

6. Calibration system (10) according to claim 5, characterized in that the optically transparent material is a glass, a glass ceramics or a plastic, in particular a lanthanum phosphate glass, a fluor phosphate glass, a crown glass, a lanthanum glass, a glass ceramics formed of these glasses, or a lithium aluminum silicate glass ceramics.

7. Calibration system (10) according to claim 4, characterized in that the at least one fluorophore is at least one metal ion, selected from the group of the rare earth metals, in particular the lanthanides, or a mixture thereof.

8. Calibration system (10) according to claim 4, characterized in that the at least one fluorophore is at least one metal ion selected from the group of the transition metals, in particular cobalt, chromium and manganese.

9. Calibration system (10) according to claim 4, characterized in that the fluorophore is selected from the group of fluorescing organic compounds, quantum dots or florescent nanocrystals.

10. Calibration system (10) according to claim 1, characterized in that the at least one calibration module (24) includes a module for determining to the intensity of the excitation light, in particular a scatterer or a glass or plastic matrix, with a bleachable fluorophore having a known bleaching kinetics.

11. Calibration system (10) according to claim 1, characterized in that the at least one calibration module (24) includes a module, in particular a scatterer, for determining the suppression of the excitation wavelength in the emission channel of the luminescence measurement system.

12. Calibration system (10) according to claim 8, characterized in that the at least one calibration module (24) comprises a module for determining the spatial resolution in the x, y, and/or z-direction and/or the illumination uniformity, in particular a reflecting and/or fluorescing surface, preferably a reflecting or fluorescing inclined plane.

13. Calibration system (10) according to claim 1, characterized in that the at least one calibration module (24) comprises a module for determining the spatial resolution in the x, y, and/or z-direction, in particular a three-dimensionally structured plane.

14. Multi-functional calibration system (10) for characterizing luminescence measurement systems, in particular spectrally resolving, wide-field and/or confocal imaging systems, comprising
(a) a baseplate (12),
(b) at least one calibration module (24) arranged on the baseplate (12) and including at least one calibration and/or characterization function, and
(c) at least one focusing device (20) integrated in the baseplate (12) with a highly planar focusing surface (22) having reflecting and/or lumenescing properties for setting a defined measurement beam focus of the luminescence measurement systems to be calibrated, the focusing surface (22) arranged in a common plane with the at least one calibration module (24) and having a surface roughness less than the optical resolution of the luminescence measurement system, wherein the at least one focusing device (20) is a substrate coated with a reflecting metal layer, in particular a silicon wafer with a sputtered chromium layer.

15. Multi-functional calibration system (10) for characterizing luminescence measurement systems, in particular spectrally resolving, wide-field and/or confocal imaging systems, comprising
   (a) a baseplate (12),
   (b) at least one calibration module (24) arranged on the baseplate (12) and including at least one calibration and/or characterization function, and
   (c) at least one focusing device (20) integrated in the baseplate (12) with a highly planar focusing surface (22) having reflecting and/or lumenescing properties for setting a defined measurement beam focus of the luminescence measurement systems to be calibrated, the focusing surface (22) arranged in a common plane with the at least one calibration module (24) and having a surface roughness less than the optical resolution of the luminescence measurement system, wherein the at least one focusing device (20) is a substrate coated with a lumenescing material, in particular a wafer with a sputtered fluorescing material, preferably with quantum dots.

16. Multi-functional calibration system (10) for characterizing luminescence measurement systems, in particular spectrally resolving, wide-field and/or confocal imaging systems, comprising
   (a) a baseplate (12),
   (b) at least one calibration module (24) arranged on the baseplate (12) and including at least one calibration and/or characterization function, and
   (c) at least one focusing device (20) integrated in the baseplate (12) with a focusing surface (22) for setting a defined measurement beam focus of the luminescence measurement systems to be calibrated, the focusing surface (22) arranged in a common plane with the at least one calibration module (24), wherein the at least one calibration module (24) can be releasably connected with the baseplate (12), in particular releasably inserted into a recess (18) of the baseplate (12).

17. A kit comprising at least a baseplate (12), with at least one focusing device (20) integrated in the baseplate (12) with a highly planar focusing surface (22) having reflecting and/or lumenescing properties for setting a defined measurement beam focus of a luminescence system to be calibrated, wherein the focusing surface has a surface roughness less than an optical resolution of the luminescence system, and a set of different calibration modules with different calibration and/or characterization functions, wherein the focusing surface is arranged in a common plane with at least one calibration module of the set of different calibration modules.

* * * * *

UNITED STATES PATENT AND TRADEMARK OFFICE
CERTIFICATE OF CORRECTION

PATENT NO. : 7,544,926 B2
APPLICATION NO. : 11/377593
DATED : June 9, 2009
INVENTOR(S) : Ute Resch-Genger It is certified that error appears in the above-identified patent and that said Letters Patent is hereby corrected as shown below:

Title Page, Item [73], the Assignee:

"Bam Bundesanstalt Fuer MaterialForschung und-Pruefung" should read

-- BAM Bundesanstalt für Materialforschung und –`prüfung --.

Signed and Sealed this

Twenty-fifth Day of May, 2010

David J. Kappos
*Director of the United States Patent and Trademark Office*